United States Patent [19]

Kansas

[11] Patent Number: 4,932,967
[45] Date of Patent: Jun. 12, 1990

[54] INTRAOCULAR LENS IMPLANT

[76] Inventor: Peter G. Kansas, 101 Murray Ave., Delmar, N.Y. 12054

[21] Appl. No.: 253,066

[22] Filed: Sep. 30, 1988

[51] Int. Cl.⁵ .............................................. A61F 2/16
[52] U.S. Cl. .................................................... 623/6
[58] Field of Search ............................................ 623/6

[56] References Cited

U.S. PATENT DOCUMENTS

| | | |
|---|---|---|
| 4,249,271 | 2/1981 | Poler . |
| 4,418,431 | 12/1983 | Feaster . |
| 4,502,162 | 3/1985 | Gerhard et al. . |
| 4,504,981 | 3/1985 | Walman . |
| 4,542,541 | 9/1985 | Pannu . |
| 4,562,600 | 1/1986 | Ginsberg et al. ............ 623/6 |
| 4,585,455 | 4/1986 | Blackmore et al. .......... 623/6 |
| 4,588,405 | 5/1986 | Knolle, Jr. . |
| 4,624,670 | 11/1986 | Bechert, II ................... 623/6 |

FOREIGN PATENT DOCUMENTS

| | | | |
|---|---|---|---|
| 0195881A | 10/1986 | European Pat. Off. ........... 623/6 |
| 2581535 | 11/1986 | France ............................... 623/6 |
| 2171912 | 9/1986 | United Kingdom ............... 623/6 |
| 84/01709 | 5/1984 | World Int. Prop. O. .......... 623/6 |

OTHER PUBLICATIONS

Lester Posterior Chamber Lens, Advertisement for Model Intermedics Intraocular, Inc., P.O. Box 70670, Pasadena, CA.
Model 120 Feaster Dualens, Advertisement Coburn Professional Products Div., P.O. Box 2498, Clearwater, FL 33517.
Intraocular Lenses from the Precision-Cosmet Collection, Advertisement-Precision-Cosmet Co., Inc., 11140 Bren Rd., Minnetonka, MN 55434, Bechert 7mm Lightweight Lens.

Primary Examiner—Randall L. Green
Assistant Examiner—Stephanie L. Iantorno
Attorney, Agent, or Firm—Hayes & Reinsmith

[57] ABSTRACT

An intraocular lens implant is provided having an optical lens and lens positioning and supporting haptics one of which has a pair of protrusions between opposite ends of an outer segment of the haptic which protrusions provide spaced discrete focal points of contact intermediate the length of the haptic segment and which cooperate with a broad arc formed by the other haptic for continuous surface-to-surface contact and improved centration and enhanced fixation upon implantation in an eye.

12 Claims, 1 Drawing Sheet

INTRAOCULAR LENS IMPLANT

FIELD OF THE INVENTION

This invention generally relates to an intraocular lens implant suited for use as an artificial lens implant in a chamber of an eye and specifically concerns such intraocular lens implants having outwardly projecting, positioning and supporting members of a significantly improved design for facile trouble-free implantation.

BACKGROUND OF THE INVENTION

An intraocular lens is employed as a replacement for a human crystaline lens and is generally of two types, those that are placed in an anterior chamber of an eye, i.e., between its iris and cornea, and those that are placed in a posterior chamber, i.e., behind the iris. Intraocular lens implants normally include an optic with two or more positioning and supporting members or haptics which extend from the optic and engage tissue of an eye requiring such an artificial lens. The optic normally comprises a circular transparent optical lens body. The haptics may be of widely varying styles and construction depending upon the intended location of the haptics, their fixation points within the eye chamber, and whether the eye itself has undergone extracapsular cataract surgery or intracapsular cataract surgery.

An aim of achieving stable fixation of such intraocular lens implants is continuously sought to ensure visual rehabilitation without postoperative complications or tissue irritation following implantation.

Accordingly, a primary object of this invention is to provide a new and improved intraocular lens implant having a haptic design featuring sufficient flexibility for the stable positioning and supporting of a lens in a desired operative position within a human eye.

Another object of this invention is to provide such an implant which is readily adapted to be manufactured in a quick and easy manner at reasonable cost.

Yet another object of this invention is to provide such an implant which provides both enhanced centration and enhanced fixation during implantation and which features a design configuration which promotes more certain and easier intraocular insertion and placement during surgery.

A further object of this invention is to provide such an implant with a haptic configuration which provides improved snag-resistance while permitting one-handed manipulation of the implant, leaving the surgeon with a free hand to perform ancillary supportive movements.

Other objects will be in part obvious and in part pointed out in more detail hereinafter.

SUMMARY OP THE INVENTION

An intraocular lens implant for eyes constructed in accordance with this invention comprises a generally circular optical lens having a pair of resiliently deformable haptics for fixing and supporting the lens in an eye, the haptics extending generally in opposite directions from diametrically opposed regions of the lens for flexure radially of the lens, the haptics each having an outer haptic segment extending along an arc generally concentric to the lens, one of the outer haptic segments having a pair of protrusions formed thereon, the protrusions extending outwardly relative to the lens beyond a projection of said arc containing said one outer haptic segment, the protrusions forming spaced discrete focal points of contact intermediate the length of said one outer haptic segment, the other outer haptic segment being configured to extend in an uninterrupted arcuate form, the protrusions on said one outer haptic segment cooperating with a broad arc of contact formed by the other outer haptic segment to provide improved centration and enhanced fixation upon implantation in an eye.

A better understanding of the objects, advantages, features, properties and relations of the invention will be obtained from the following detailed description and accompanying drawing which set forth an illustrative embodiment and is indicative of the way in which the principle of the invention is employed.

DETAILED DESCRIPTION OF A PREFERRED EMBODIMENT

Figure 1:
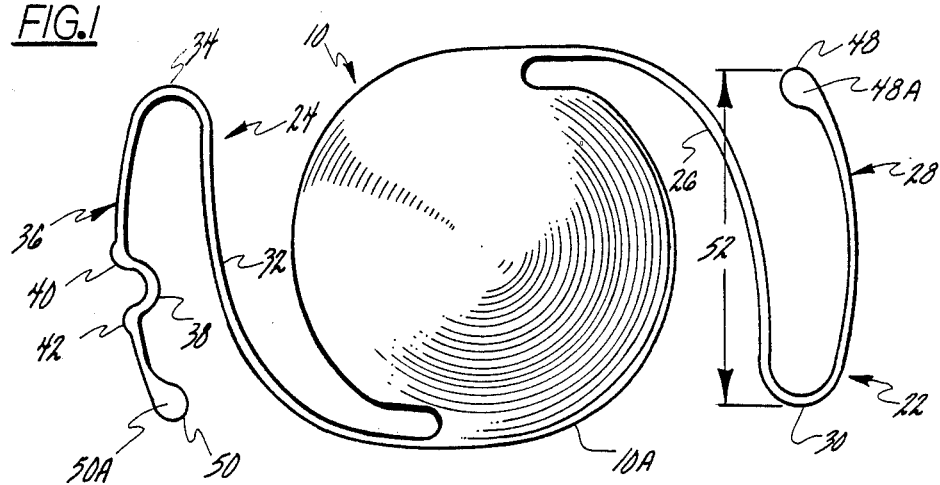
FIG. 1 is a front view of an intraocular lens implant incorporating this invention.
Figure 4:
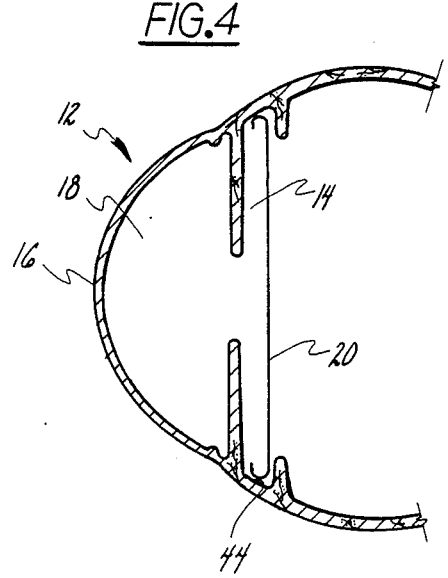
FIG. 4 is a cross-sectional schematic view of an eye with its normal lens removed.

Referring to FIG. 1, an intraocular lens implant 10 is illustrated and will be understood to be particularly suited for implantation in a human eye such as shown at 12 (FIG. 4), particularly in a posterior chamber 14 of eye 12. Eye 12 includes a cornea 16 through which light is transmitted to pass through an anterior chamber 18 and the fluid within that chamber whereupon the light would normally have impinged upon a crystaline lens (not shown) serving as a focusing device for light to impinge upon a retina, not shown. The lens normally is encased within a sac, which is shown in part at 20 which will be understood to be what remains as the lens capsule in an extracapsular eye following surgery wherein at least part of the capsular tissue is left intact within eye 12 (in contrast, intracapsular surgery involves removal of the crystaline lens together with its supporting capsular tissue.) In either event, surgical removal of the crystaline lens results in the loss of the ability of the eye to focus and, hence, the necessity for an artificial lens implant or lens 10.

The lens 10 is shown having a generally circular plano-convex body 10A and may be molded, if desired, from a clear polymeric material such as a polymethylmethacrylate or other suitable biocompatible, non-absorbable and non-toxic material.

Lens 10 is shown also having a pair of resiliently deformable haptics 22,24 of generally circular cross-section for fixing and supporting lens 10 in an eye 12. These haptics 22,24 and optical lens 10 may be of one-piece construction or integrally formed from separate pieces with the haptics firmly inserted into openings (not shown) formed in the optical lens. Haptics 22,24 extend symmetrically from opposite sides of the periphery of lens 10 in opposite directions. Haptic 22 is shown as having an inner segment 26 connected to the lens 10, a reversely oriented outer segment 28 and a u-shaped connecting segment 30 joining the inner and outer segments 26,28. The outer segment 28 extends along an arc generally concentric to lens 10.

Haptic 24 is formed with an inner segment 32 and a connecting segment 34 which are identical but in mirror image relation to their corresponding segments 26 and 30 of haptic 22. In accordance with one feature of this invention, the outer segment 36 of haptic 24 includes an outwardly opening notch 38 intermediate the length of the outer haptic segment 36 between its opposite ends and features a pair of protrusions 40,42 formed on haptic 24.

More specifically, protrusions 40,42 act to prevent decentration during implantation and to provide positive resistance to undesired rotation. Protrusions 40, 42 thus provide discrete focal points of contact or points of fixation with either capsular tissue 20 or ciliary sulcus tissue 44 (FIG. 1) in the case of intracapsular surgery, thereby enhancing stabilization and providing more secure fixation. The protrusions 40,42 are each formed, as best seen in FIG. 3, to project beyond an arc illustrated in broken lines at 46, which arc contains the adjacent portions 36A, 36B of the outer haptic segment 36 on opposite sides of notch 38 in the illustrated normally relaxed condition of the haptic segment 36, thereby insuring the effectiveness of the protrusions 40, 42 as focal contact points during fixation of the implant.

Figure 3:
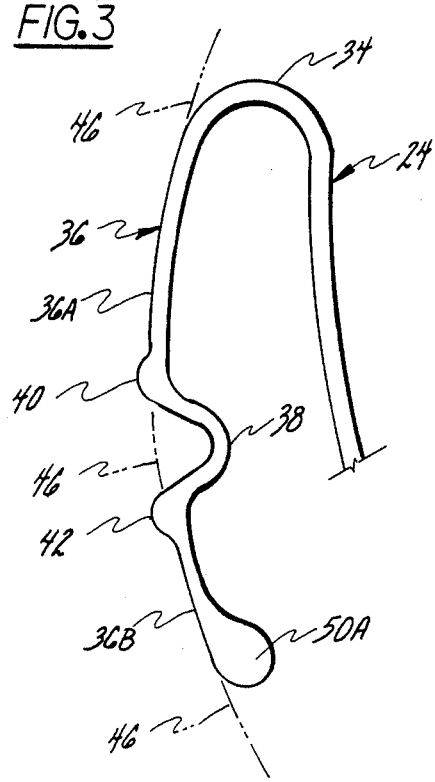
FIG. 3 is an enlarged view, partly broken away, of a portion of a haptic of the implant of FIG. 1.

By virtue of the described construction, protrusions 40,42 of outer haptic segment 36 cooperate with adjacent portions 36A, 36B and provide discrete point contact engagement with the ocular tissue adjacent its surface-to-surface engagement provided by portions 36A and 36B (FIG. 3). Jointly cooperating with outer haptic segment 36 is the entire outer segment 28 of haptic 22. Segment 28 as disclosed is configured to provide a continuously curved arc or length of material for uninterrupted surface-to-surface contact with the tissue surface within eye 12 which is contacted upon implantation.

Figure 2:
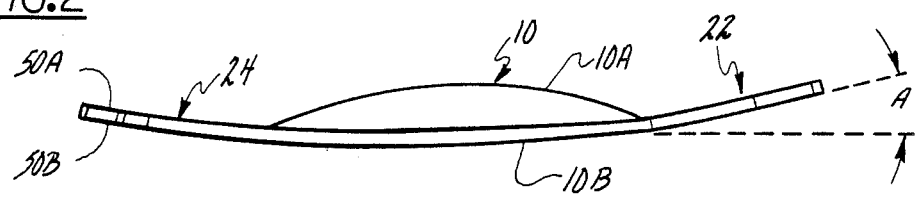
FIG. 2 is a side elevational view of the implant of FIG. 1.

As best seen in FIG. 2, the haptics 22,24 each are formed with their inner segment 26,32 connected to lens 10 and extend from opposite sides of the periphery of the lens 10 in opposite directions with each haptic 22,24 disposed on a common side of a planar surface 10B of the lens. The reversely curved haptic configuration is particularly suited to be adjusted to provide an expansive tension upon being compressed during implantation for preventing undesired displacement while maintaining centration of the lens. The haptics 22,24 are shown respectively contained in planes each extending at a common predetermined angle (shown as "A" in FIG. 2) relative to the planar surface 10B of lens 10 for directing forces of the haptics posteriorly to the lens 10 during expansion and fixation of the haptics upon their being engaged with the ocular tissue.

In accordance with another aspect of this invention, the haptics 22,24 each have a free terminal end 48, 50, a portion of which is of enlarged cross-section forming a snag-resistant, solid broadened tip directed radially inwardly toward the lens 10. The tip of each free terminal end have opposite major surfaces, such as shown at 48A, 50A and 50B extending generally radially of the lens 10 and contained in the same planes containing haptics 22, 21.

It accordingly will be seen that the intraocular lens implant of this invention is particularly suited for implantation in a posterior chamber of an eye either in engagement with capsular tissue or ciliary sulcus tissue. The disclosed structure features free terminal ends of haptics which are snag-resistant, less bulky and less space occupying and which, accordingly, do not interfere with insertion when the haptics are maximally compressed against the optical lens 10 during intraocular placement. Such compression is accomplished in a conventional manner by a surgeon to bend the resiliently deformable haptics 22,24 toward the optical lens 10 without flexing the lens. To insure that the haptics 22, 24 will not overlap and extend beyond the edges of the optical lens 10 during such compression, or otherwise interfere with its visualization or with placement of the implant during surgery, the chordal length (dimension 52 in FIG. 1) between opposite ends of the outer haptic segments 28, 36 are each slightly less than 6.0 millimeters (when in a relaxed condition as viewed in the drawing) which is less than the diameter of the optical lens, preferably of 6.5 millimeters. Accordingly, the reduced chordal dimension of the outer haptic segments (such as at 52) enhances the contact between ocular tissues and the haptics and allows for more certain and easier insertion and placement because it is a smaller dimension than the optical lens 10. Moreover, the concentricity of the outer haptic segments 28, 36 relative to lens 10 provides a more compact construction which is easy to manipulate during surgery.

As will be apparent to persons skilled in the art, various modifications, adaptations and variations of the foregoing specific disclosure can be made without departing from the teaching of this invention.

I claim:

1. An intraocular lens implant for an eye and comprising a generally circular optical lens having a pair of resiliently deformable haptics for fixing and supporting the lens in an eye, the haptics extending generally in opposite directions from diametrically opposed regions of the lens for flexure radially of the lens, the haptics each having an outer haptic segment extending along an arc generally concentric to the lens, one of the outer haptic segments having a pair of protrusions formed thereon, the protrusions of said one haptic segment in its normal relaxed condition extending outwardly relative to the lens beyond a projection of said arc containing said one outer haptic segment, the protrusions forming spaced discrete focal points of contact intermediate the length of said one outer haptic segment, the other out haptic segment being configured to extend in an uninterrupted arcuate form, the protrusions on said one outer haptic segment cooperating with a broad arc of contact formed by the other outer haptic segment to provide improved centration and enhanced fixation upon implantation in an eye, and wherein said pair of protrusions are formed to project solely in a direction extending outwardly relative to the lens and are contained in their entirety within planes containing the outer segment of said one haptic.

2. The intraocular lens implant of claim 1 wherein said one outer haptic segment further includes a notch formed intermediate its length, the notch having an opening directed outwardly relative to the lens, and wherein the protrusions are formed at opposite ends of the notch.

3. The intraocular lens implant of claim 1 wherein the lens includes a planar surface, wherein the haptics are each disposed on a common side of the planar surface of the lens, and wherein the haptics are respectively contained in planes extending at a common predetermined angle relative to said planar surface of the lens.

4. The intraocular lens implant of claim 1 wherein the outer haptic segments each have a free terminal end of enlarged cross-section forming a broadened tip thereon.

5. The intraocular lens implant of claim 4 wherein the tip of the free terminal end has a rounded edge.

6. The intraocular lens implant of claim 4 wherein the tip of the free terminal end is directed radially inwardly toward the lens and is of a solid compact form having teardrop-shaped major surfaces.

7. The intraocular lens implant of claim 4 wherein the tip of the free terminal end has opposite major surfaces of flat contour extending generally radially of the lens.

8. The intraocular lens implant of claim 1 wherein the haptics are each reversely curved to form said outer haptic segment, and wherein a chordal dimension of each outer haptic segment between its opposite ends is less than the diameter of the lens.

9. The intraocular lens implant of claim 8 wherein the lens has a diameter of 6.5 millimeters, and wherein the length of the chordal dimension between opposite ends of each outer haptic segment is not more than 6.0 millimeters.

10. The intraocular lens implant of claim 1 wherein the lens and its haptics are integrally formed as a single-piece unit.

11. The intraocular lens implant of claim 1 wherein each haptic has a free terminal end on its outer segment including a snag-resistant tip of enlarged size with opposite major surfaces of flat contour with a rounded edge, the tip of each haptic being directed radially inwardly toward the lens, and wherein a chordal dimension of each outer haptic segment between its opposite ends is less than the diameter of the lens.

12. An intraocular lens implant for an eye and comprising a generally circular plano-convex optical lens having a pair of resiliently deformable haptics for fixing and supporting the lens in an eye, the haptics symmetrically extending from opposite sides of the periphery of the lens in opposite directions, the haptics each having an inner segment connected to the lens, a reversely oriented outer segment and a u-shaped connecting segment joining adjacent portions of its inner and outer segments, the outer segments each extending along an arc generally concentric to the lens, the outer segment of one of the haptics having a notch intermediate its length with the notch opening outwardly relative to the lens, the outer segment of said one haptic having a pair of protrusions formed thereon on opposite ends of said notch and extending solely outwardly relative to the lens beyond a projection of said arc containing adjacent portions of the outer segment of said one haptic in its relaxed condition, the protrusions forming spaced discrete focal points of contacts, the outer segment of the other haptic being configured to provide a continuous length of uninterrupted surface contact with tissue surface within the eye which it contacts upon implantation thereby to cooperate with the two focal points of contact provided by the protrusions of said one haptic for enchanced fixation and improved centration.

* * * * *

UNITED STATES PATENT AND TRADEMARK OFFICE
CERTIFICATE OF CORRECTION

PATENT NO. : 4,932,967
DATED : June 12, 1990
INVENTOR(S) : Peter G. Kansas

It is certified that error appears in the above-identified patent and that said Letters Patent is hereby corrected as shown below:

Column 3 - Line 12 as reads "(FIG. 1)" should read --(FIG. 4)--

Column 3 - Line 58 as reads "22, 21" should read --22, 24--

Column 4 - Line 41 as reads "out" should read --outer--

Signed and Sealed this

Eighteenth Day of August, 1992

*Attest:*

DOUGLAS B. COMER

*Attesting Officer*     *Acting Commissioner of Patents and Trademarks*